United States Patent [19]
Hammerstedt et al.

[11] Patent Number: 6,004,586
[45] Date of Patent: Dec. 21, 1999

[54] MOLECULE INVOLVED IN BINDING OF SPERM TO EGG SURFACES AND PROCEDURES FOR USE OF THIS MOLECULE TO ENHANCE OR DECREASE POTENTIAL FERTILITY

[75] Inventors: Roy H. Hammerstedt, Boalsburg; Palmer G. Cramer; Guy F. Barbato, both of State College, all of Pa.

[73] Assignee: The Penn State Research Foundation, University Park, Pa.

[21] Appl. No.: 09/027,376

[22] Filed: Feb. 20, 1998

Related U.S. Application Data

[62] Division of application No. 08/584,671, Jan. 11, 1996, Pat. No. 5,910,568.

[51] Int. Cl.[6] .......................... A61K 32/52; A61K 35/54; A01N 37/18; C07K 1/00
[52] U.S. Cl. .......................... 424/561; 424/581; 424/582; 514/2; 530/395; 530/402; 530/850; 530/851; 530/852; 530/853
[58] Field of Search .................................. 435/7.1, 2, 29, 435/284.1, 806, 7.92–7.95, 69.1; 530/300, 324, 325, 350, 387.1, 412, 850, 851, 852, 853, 395, 402; 424/561, 581, 582; 514/2

[56] References Cited

FOREIGN PATENT DOCUMENTS 9503821  9/1995  WIPO .

OTHER PUBLICATIONS

Cramer et al. Biology of Reproduction May 1994, vol. 50 (5) Abstract 293.
Collard et al. Biochemstry 1988 vol. 27, 4557–5464.

*Primary Examiner*—Anthony C. Caputa
*Assistant Examiner*—Mark Navarro
*Attorney, Agent, or Firm*—Webb Ziesenheim Logsdon Orkin & Hanson, P.C.

[57] ABSTRACT

A purified polypeptide which provides for initial binding of sperm to oocyte investments and has an active amino acid sequence of SEQ ID NO:12 (Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Arg-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys); or SEQ ID NO:13 (Cys-Glu-Ser-Leu-Gln-Lys-His-Leu-Ala-Glu-Leu-Asn-His-Gln-Lys-Gln-Leu-Glu-Ser-Asn-Lys-Ile-Pro-Glu-Leu-Asp-Met-Thr-Glu-Val-Val-Ala-Pro-Phe-Met-Ala-Asn-Ile-Pro-Leu-Leu-Leu-Tyr-Pro-Gln-Asp-Gly-Pro-Arg-Ser-Lys-Pro-Gln-Pro-Lys-Asp-Asn-Gly-Asp-Val-Cys); or the shorter but biologically active SEQ ID NO:1 and SEQ ID NO:9 (Tyr-Pro-Gln-Asp-Arg-X-Arg-Ser-Gln-Pro-Gln-Pro-Lys-Ala-Asn, where X is Thr or Pro). The polypeptide is useful in improving sperm-egg binding by fresh sperm, restoring sperm-egg binding following a cryo-preservation cycle, enhancing fertilizing potential, and producing antibodies to determine fertilizing potential of sperm, determining sperm-binding sites on egg investments, and contraception.

10 Claims, 8 Drawing Sheets

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
      (A) LENGTH: 15

(B) TYPE: AMINO ACID (C) STRANDEDNESS: SINGLE (D) TOPOLOGY: UNKNOWN (xi) SEQUENCE DESCRIPTION: SEQ ID NO: 1:

Tyr Pro Gln Asp Arg Thr Arg Ser Gln Pro Gln Pro Lys
1               5                   10

Ala Asn
    15

(3) INFORMATION FOR SEQ ID NO: 2:

(i) SEQUENCE CHARACTERISTICS:
      (A) LENGTH: 12

(B) TYPE: AMINO ACID (C) STRANDEDNESS: SINGLE (D) TOPOLOGY: UNKNOWN (xi) SEQUENCE DESCRIPTION: SEQ ID NO: 2:

Tyr Pro Gln Asp Arg Thr Arg Ser Gln Pro Gln Pro
1               5                   10

(4) INFORMATION FOR SEQ ID NO: 3:

(i) SEQUENCE CHARACTERISTICS:
      (A) LENGTH: 7

(B) TYPE: AMINO ACID (C) STRANDEDNESS: SINGLE (D) TOPOLOGY: UNKNOWN (xi) SEQUENCE DESCRIPTION: SEQ ID NO: 3:

Gln Pro Gln Pro Lys Ala Asn
1               5

(5) INFORMATION FOR SEQ ID NO: 4:

(i) SEQUENCE CHARACTERISTICS:
      (A) LENGTH: 15

(B) TYPE: AMINO ACID (C) STRANDEDNESS: SINGLE (D) TOPOLOGY: UNKNOWN (xi) SEQUENCE DESCRIPTION: SEQ ID NO: 4:

Gln Pro Gln Pro Lys Ala Asn Glu Asp Val Cys Gln Asp

-continued

```
1               5                   10

Cys Met
        15

(6)  INFORMATION FOR SEQ ID NO: 5:

(i)  SEQUENCE CHARACTERISTICS:
          (A)  LENGTH: 19

(B)  TYPE: AMINO ACID (C)  STRANDEDNESS: SINGLE (D)  TOPOLOGY: UNKNOWN (xi) SEQUENCE DESCRIPTION: SEQ ID NO: 5:

Pro Gln Pro Lys Ala Asn Glu Asp Val Cys Gln Asp Cys
1               5                   10

Met Lys Leu Val Thr Asp
        15

(7)  INFORMATION FOR SEQ ID NO: 6:

(i)  SEQUENCE CHARACTERISTICS:
          (A)  LENGTH: 12

(B)  TYPE: AMINO ACID (C)  STRANDEDNESS: SINGLE (D)  TOPOLOGY: UNKNOWN (xi) SEQUENCE DESCRIPTION: SEQ ID NO: 6:

Tyr Pro Gln Asp Arg Thr Arg Ser Gln Pro Gln Cys
1               5                   10

(8)  INFORMATION FOR SEQ ID NO: 7:

(i)  SEQUENCE CHARACTERISTICS:
          (A)  LENGTH: 12

(B)  TYPE: AMINO ACID (C)  STRANDEDNESS:  SINGLE (D)  TOPOLOGY: UNKNOWN (xi) SEQUENCE DESCRIPTION: SEQ ID NO: 7:

Xaa Pro Gln Asp Arg Thr Arg Ser Gln Pro Gln Pro
1               5                   10

(9)  INFORMATION FOR SEQ ID NO: 8:

(i)  SEQUENCE CHARACTERISTICS:
          (A)  LENGTH: 14

(B)  TYPE: AMINO ACID (C)  STRANDEDNESS:  SINGLE (D)  TOPOLOGY:  UNKNOWN (xi) SEQUENCE DESCRIPTION:  SEQ ID NO: 8:

Phe Phe Tyr Pro Gln Asp Arg Thr Arg Ser Gln Pro Gln
1               5                   10
```

Pro

(10) INFORMATION FOR SEQ ID NO: 9:

(i) SEQUENCE CHARACTERISTICS:
        (A) LENGTH: 15

(B) TYPE: AMINO ACID (C) STRANDEDNESS: SINGLE (D) TOPOLOGY: UNKNOWN (xi) SEQUENCE DESCRIPTION: SEQ ID NO: 9:

Tyr Pro Gln Asp Arg Pro Arg Ser Gln Pro Gln Pro Lys
1               5                  10

Ala Asn
    15

(11) INFORMATION FOR SEQ ID NO: 10:

(i) SEQUENCE CHARACTERISTICS:
        (A) LENGTH: 16

(B) TYPE: AMINO ACID (C) STRANDEDNESS: SINGLE (D) TOPOLOGY: UNKNOWN (xi) SEQUENCE DESCRIPTION: SEQ ID NO: 10:

Leu Tyr Pro Gln Asp Arg Thr Arg Ser Gln Pro Gln Pro
1               5                  10

Lys Ala Asn
    15

(12) INFORMATION FOR SEQ ID NO: 11:

(i) SEQUENCE CHARACTERISTICS:
        (A) LENGTH: 16

(B) TYPE: AMINO ACID (C) STRANDEDNESS: SINGLE (D) TOPOLOGY: UNKNOWN (xi) SEQUENCE DESCRIPTION: SEQ ID NO: 11:

Xaa Tyr Pro Gln Asp Arg Thr Arg Ser Gln Pro Gln Pro
1               5                  10

Lys Ala Asn
    15

(13) INFORMATION FOR SEQ ID NO: 12

(i) SEQUENCE CHARACTERISTICS:
        (A) LENGTH: 60

(B) TYPE: AMINO ACID (C) STRANDEDNESS: SINGLE (D) TOPOLOGY: UNKNOWN (xi) SEQUENCE DESCRIPTION: SEQ ID NO: 12:

Cys Gln Ser Leu Gln Glu Tyr Leu Ala Glu Gln Asn Gln
1               5                  10

Arg Gln Leu Glu Ser Asn Lys Ile Pro Glu Val Asp Leu
    15                  20                  25

Ala Arg Val Val Ala Pro Phe Met Ser Asn Ile Pro Leu
            30                  35

Leu Leu Tyr Pro Gln Asp Arg Pro Arg Ser Gln Pro Gln
40              45                  50

Pro Lys Ala Asn Glu Asp Val Cys
        55                  60

(14) INFORMATION FOR SEQ ID NO: 13:

(i) SEQUENCE CHARACTERISTICS:
         (A) LENGTH: 61

(B) TYPE: AMINO ACID (C) STRANDEDNESS: SINGLE (D) TOPOLOGY: UNKNOWN (xi) SEQUENCE DESCRIPTION: SEQ ID NO: 13:

Cys Glu Ser Leu Gln Lys His Leu Ala Glu Leu Asn His
1               5                  10

Gln Lys Gln Leu Glu Ser Asn Lys Ile Pro Glu Leu Asp
    15                  20                  25

Met Thr Glu Val Val Ala Pro Phe Met Ala Asn Ile Pro
            30                  35

Leu Leu Leu Tyr Pro Gln Asp Gly Pro Arg Ser Lys Pro
40              45                  50

Gln Pro Lys Asp Asn Gly Asp Val Cys
        55                  60

(15) INFORMATION FOR SEQ ID NO: 14:

(i) SEQUENCE CHARACTERISTICS:
         (A) LENGTH: 79

(B) TYPE: AMINO ACID (C) STRANDEDNESS: SINGLE (D) TOPOLOGY: UNKNOWN (xi) SEQUENCE DESCRIPTION: SEQ ID NO: 14:

Pro Gly Glu Val Cys Ala Leu Asn Leu Cys Gln Ser Leu
1               5                  10

Gln Glu Tyr Leu Ala Glu Gln Asn Gln Arg Gln Leu Glu
    15                  20                  25

Ser Asn Lys Ile Pro Glu Val Asp Leu Ala Arg Val Val
            30                  35

Ala Pro Phe Met Ser Asn Ile Pro Leu Leu Leu Tyr Pro
40              45                  50

Gln Asp Arg Pro Arg Ser Gln Pro Gln Pro Lys Ala Asn
        55                  60                  65

Glu Asp Val Cys Gln Asp Cys Met Lys Leu Val Thr Asp
            70                  75

Ile

(16) INFORMATION FOR SEQ ID NO: 15:

(i) SEQUENCE CHARACTERISTICS:
        (A) LENGTH: 80

(B) TYPE: AMINO ACID (C) STRANDEDNESS: SINGLE (D) TOPOLOGY: UNKNOWN (xi) SEQUENCE DESCRIPTION: SEQ ID NO: 15:

```
Pro Gly Glu Val Cys Ala Leu Asn Leu Cys Glu Ser Leu
 1               5                  10

Gln Lys His Leu Ala Glu Leu Asn His Gln Lys Gln Leu
         15              20              25

Glu Ser Asn Lys Ile Pro Glu Leu Asp Met Thr Glu Val
             30              35

Val Ala Pro Phe Met Ala Asn Ile Pro Leu Leu Leu Tyr
 40                  45              50

Pro Gln Asp Gly Pro Arg Ser Lys Pro Gln Pro Lys Asp
         55              60              65

Asn Gly Asp Val Cys Gln Asp Cys Ile Gln Met Val Thr
                 70              75

Asp Ile
     80
```

(17) INFORMATION FOR SEQ ID NO: 16:

(i) SEQUENCE CHARACTERISTICS:
        (A) LENGTH: 79

(B) TYPE: AMINO ACID (C) STRANDEDNESS: SINGLE (D) TOPOLOGY: UNKNOWN (xi) SEQUENCE DESCRIPTION: SEQ ID NO: 16:

```
Pro Gly Glu Val Cys Ala Leu Asn Leu Cys Gln Ser Leu
 1               5                  10

Gln Glu Tyr Leu Ala Glu Gln Asn Gln Lys Gln Leu Glu
         15              20              25

Ser Asn Lys Ile Pro Glu Val Asp Met Ala Arg Val Val
             30              35

Ala Pro Phe Met Ser Asn Ile Pro Leu Leu Leu Tyr Pro
 40                  45              50

Gln Asp His Pro Arg Ser Gln Pro Gln Pro Lys Ala Asn
         55              60              65

Glu Asp Val Cys Gln Asp Cys Met Lys Leu Val Ser Asp
                 70              75

Val
```

MOLECULE INVOLVED IN BINDING OF SPERM TO EGG SURFACES AND PROCEDURES FOR USE OF THIS MOLECULE TO ENHANCE OR DECREASE POTENTIAL FERTILITY

RELATED APPLICATION

The present application is a divisional application of U.S. patent application Ser. No. 08/584,671, filed Jan. 11, 1996, now U.S. Pat. No. 5,910,568.

FIELD OF THE INVENTION

This invention relates to sperm-egg binding proteins and their uses.

BACKGROUND OF THE INVENTION

Assisted reproductive technologies such as artificial insemination have been practiced commercially with livestock and horses for almost a century, and with poultry, humans and other species for almost a half century. Artificial insemination requires a sample of semen consisting of spermatozoa produced by the testes and seminal plasma contributed by epithelial cells of the epididymides, deferent ducts and accessory sex glands. In addition to water, seminal plasma contains numerous proteins and glycoproteins, phospholipids, lipids, sugars and other carbohydrates, and ions.

It was early recognized that those portions of seminal plasma originating from the deferent ducts and accessory sex glands are not essential for spermatozoa to acquire or to retain fertilizing capability. Furthermore, for some species, or for certain males of a species, retention of trace or moderate amounts of seminal plasma in association with the sperm is desirable for retention of fertilizing capability during storage, whereas for others seminal plasma is deleterious. The beneficial or deleterious effects of seminal plasma on sperm became increasingly evident as procedures were developed to store sperm for several hours or days at 4 to 22° C., or for years at −196° C.

It has become evident that certain proteins or glycoproteins, phospholipids, and other components of seminal plasma can be loosely bound to sperm, presumably by interaction with the glycocalyx surrounding the sperm plasma membrane, or less frequently by true incorporation into the plasma membrane. Such molecules might be involved in binding of sperm to eggs. It has been reported that a crude mixture of proteins, extracted from human sperm by treatment with 0.6 M KCl, increased the number of human sperm bound to a human zona pellucida in vitro. Jean et al., "Increased Zona-binding Ability After Incubation of Spermatozoa with Proteins Extracted from Spermatozoa of Fertile Semen", *J. of Reproduction and Fertility* (1995), Vol. 105, pp. 43–48. However, in contrast to the present invention, that protein was not obtained by freezing sperm, and that publication gives no clue to the identity of the active molecule(s), mechanism of action, or species specificity.

The initial event in the fertilization process is binding of one or more sperm to the egg investments. Most research has focused on the molecular nature of the egg coverings in mammals (zona pellucida, an acellular coating outside a mammalian oocyte, and plasma membrane) and the nature of enzymes or glycoproteins on or in the plasma membrane or acrosome of sperm in mammals and invertebrates. Little research has been done on the molecular nature of avian sperm-egg binding, especially as it relates to the "sperm side" of the interaction.

In mammals, a spermatozoon is considered to bind to the oocyte through a series of egg-binding proteins (ligands) located on the surface of the spermatozoon which interact with appropriate members of a series of sperm receptors located on the investments of the oocyte, namely the zona pellucida and oocyte plasma membrane.

Sperm-egg binding proteins generally are considered to be transmembrane proteins or glycoproteins, possibly with enzymatic activity, with an extracellular domain that interacts with a specific sperm receptor. The consensus scenario which has evolved is one of sequential binding: (a) loose binding to the zona pellucida via one or more molecules located on the sperm plasma membrane, (b) tight binding to the zona pellucida via (a) molecule(s) located on the plasma membrane and/or the acrosomal membrane, and (c) tight binding to the oocyte plasma membrane followed by fusion of the sperm and egg plasma membranes and entrance of the entire spermatozoon into the oocyte. Thus, species-specific adhesion between sperm and eggs is attributable to complexes formed between egg-binding proteins on sperm and complementary sperm receptors on eggs. Species non-specific egg-binding proteins are thought to exist, because binding to zona-free hamster oocytes occurs with sperm of many species, but at least one species-specific egg-binding protein also must be located on the sperm surface. To date, no universal class of candidate molecules has been identified as the species-non-specific, loose egg-binding component.

SUMMARY OF THE INVENTION

The present invention is a purified polypeptide (termed universal primary sperm-egg binding protein, or UPSEBP) which provides for initial bonding of sperm to oocyte investments and uses of the polypeptide. The inventive polypeptide has biological activity in a variety of avian and mammalian species and has active sites within the amino acid sequence embodied in SEQ ID NO:12 which is Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Arg-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys. One of these active sites is within the portion of the amino acid sequence embodied in SEQ ID NO:9 or Tyr-Pro-Gln-Asp-Arg-X-Arg-Ser-Gln-Pro-Gln-Pro-Lys-Ala-Asn, where X is Thr or Pro. The tertiary structure of SEQ ID NO:12 or a similar sequence affects biological activity. Uses of the synthetic or natural polypeptide include in vitro treatment of sperm to restore fertilizing capacity for some samples of thawed cryopreserved sperm or to enhance fertilizing potential of some fresh sperm, intra-vaginal treatment of sperm to enhance sperm-egg binding and increase probability of fertilization, and use in an in vitro assay to determine fertilizing potential of sperm. Antibodies to the polypeptide are also useful for in vitro assays to determine potential fertility of sperm or number of sperm-binding sites on an egg investment or in vivo as a contraceptive.

There exists a need for a universal sperm-egg binding material for use in enhancing the ability of sperm to bind loosely with an egg or other fertilization or contraception techniques.

BRIEF DESCRIPTION OF THE FIGURES

FIG. 5b shows the percentage increase in fertility resulting from treatment of sperm with UPSEBP for the 20 roosters of FIG. 5a;

DETAILED DESCRIPTION OF THE INVENTION

Figure 2:
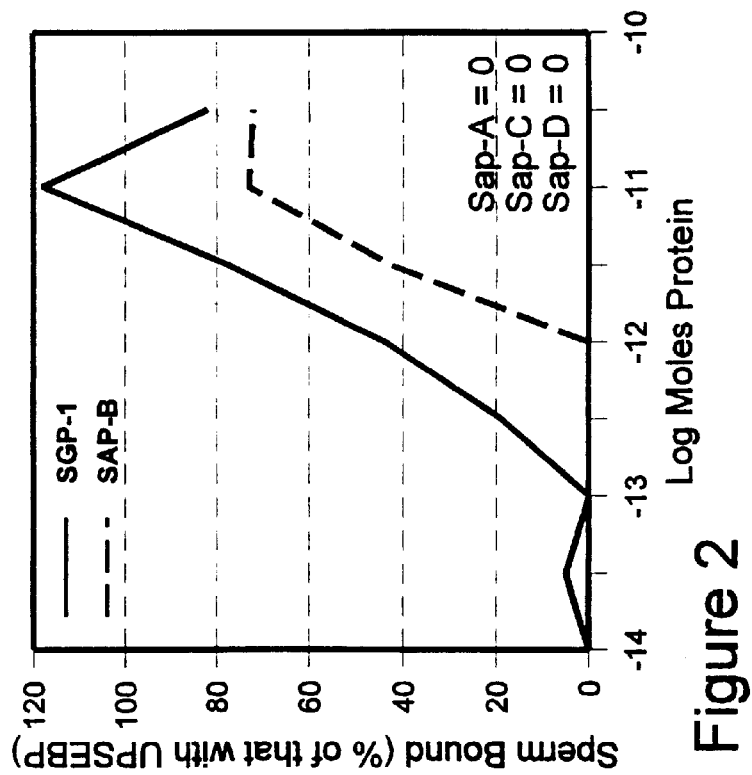
FIG. 2 compares the restorative ability of SGP-1 (prosaposin) and saposins A, B, C and D when used to treat frozen-thawed rooster sperm.
Figure 1:
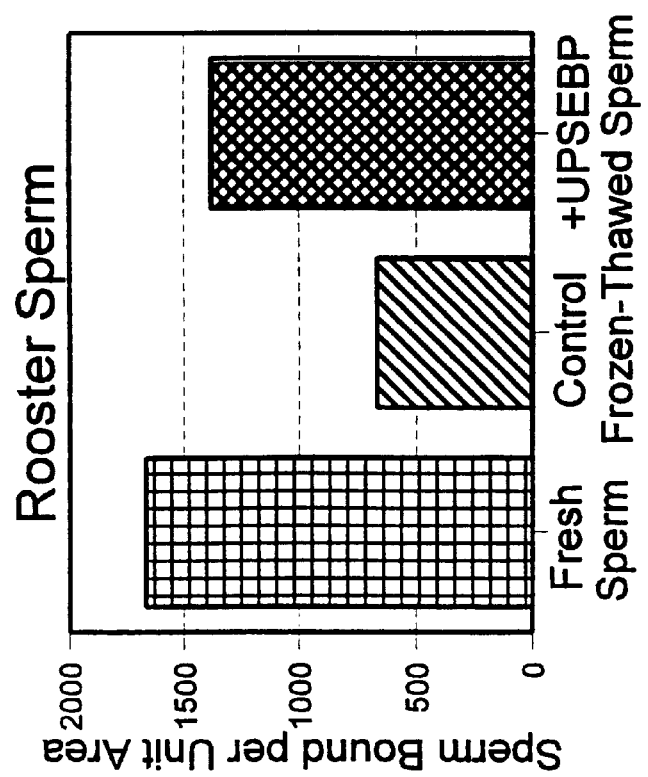
FIG. 1 compares the number of sperm bound before and after cryopreservation, treated with UPSEBP and untreated to fresh sperm.

The present invention is a native or synthetic polypeptide which provides for sperm-egg binding and the uses of the polypeptide. The polypeptide of the present invention is a member of the family of proteins including prosaposin (also termed SGP-1) and saposins. Prosaposin has been reported in human seminal plasma at 90 μg/ml and has long carbohydrate side chains. Four saposins (A, B, C, D) are produced by proteolytic cleavage of prosaposin, and individually have molecular weights of approximately 15 kilodaltons. The three residual intervening segments between saposins A, B, C and D have no known function. The parent prosaposin and processed saposins have been detected in almost every tissue examined, including the brain, testes, heart, kidney, liver, spleen, semen and milk.

The native polypeptide of this invention was purified by centrifugation of sperm suspensions frozen and thawed in the presence of 10 to 12 percent glycerol, which provided a supernatant fraction which was passed through a 300 kilodalton cut off ultrafiltration membrane. The filtrate was extracted with N-butanol: diisopropylether to remove lipid and provide a crude protein preparation. Addition of this crude protein to a suspension of frozen-thawed rooster sperm restored their ability to bind to the membrane preparations from hen's eggs. The active moiety of the native polypeptide was concentrated in the aqueous phase after lipid extraction and had an apparent molecular weight of about 10 kilodaltons.

The active molecule represented less than 0.1 percent of the crude protein recovered from the N-butanol: diisopropylether extracts, and was increased in specific activity by use of a G3000-SWXL gel filtration column followed by C4-hydrophobicity chromatography.

Hereafter, the molecule, originally isolated from rooster sperm, is termed "universal primary sperm-egg binding protein" or "UPSEBP." The amino acid sequence SEQ ID NO:1 (Tyr-Pro-Gln-Asp-Arg-Thr-Arg-Ser-Gln-Pro-Gln-Pro-Lys-Ala-Asn) was found to confer substantial binding activity as did SEQ ID NO:9 (Tyr-Pro-Gln-Asp-Arg-Pro-Arg-Ser-Gln-Pro-Gln-Pro-Lys-Ala-Asn) and SEQ ID NO:12 (Cys-Gln-Ser-Leu-Gln-Glu-Tyr-Leu-Ala-Glu-Gln-Asn-Gln-Arg-Gln-Leu-Glu-Ser-Asn-Lys-Ile-Pro-Glu-Val-Asp-Leu-Ala-Arg-Val-Val-Ala-Pro-Phe-Met-Ser-Asn-Ile-Pro-Leu-Leu-Leu-Tyr-Pro-Gln-Asp-Arg-Pro-Arg-Ser-Gln-Pro-Gln-Pro-Lys-Ala-Asn-Glu-Asp-Val-Cys). SEQ ID NO:12, which contains SEQ ID NO:9, conferred substantial binding activity especially when oxidized to form a molecule with a hairpin form. These amino acid sequences are compared in Table No. 1 with pertinent portions of the amino acid sequences of the similar rat SGP-1 (SEQ ID NO:14). Human prosaposin (SEQ ID NO:15), and mouse prosaposin (SEQ ID NO:16) also are shown in Table 1. Neither SEQ ID NO:1 nor SEQ ID NO:9 overlaps with the amino acid sequences of saposin A or saposin B, and SEQ ID NO:12 is the entire intervening sequence saposin A-B plus the terminal 6 amino acids of saposin A and the first 4 amino acids of saposin B. The biological activity of SEQ ID NO:12 or UPSEBP is distinct from those ascribed to saposin A, saposin B, or other regions of the intact prosaposin molecule. SEQ ID NO:13 is a variation of SEQ ID NO:12 and also should have high biological activity.

The biological activity of the native UPSEBP prepared from rooster sperm and synthetic amino acid sequences were compared in an in vitro assay of sperm binding described in copending U.S. patent application Ser. No. 08/234,448 abandoned. This microwell assay used plates in which the wells were coated with a binding substrate prepared from an extract of hen's egg vitelline membrane. The thawed rooster sperm, known to be reduced in UPSEBP, were washed once with isotonic salt solutions, resuspended at $50 \times 10^5/0.1$ ml, and incubated 30 minutes with 0.02–50 μg/0.5 ml native UPSEBP or synthetic peptide. Then 0.1 ml of a suspension of about $5 \times 10^6$ sperm were placed into each of triplicate wells in a microwell plate. After 2 hours of incubation at 37° C., unbound sperm were washed away and bound sperm were stained and counted using a microscope. The number of sperm bound was considered to be a measure of biological activity because there is a high correlation between the number of rooster sperm bound in vitro to such an egg extract and the fertilizing potential of sperm in that sample, as quantified by the percentage of eggs hatching young chicks after artificial insemination.

Table No. 1 presents the amino acid sequence of synthetic peptides and the resulting binding capacity as compared to native UPSEBP (full sequence not provided). Initial evaluations of the capabilities of SEQ ID NO:1 through SEQ ID NO:11, native UPSEBP and rat SGP-1 to enhance sperm binding to an egg-membrane substrate were based on visual counts of bound sperm and conducted over a number of months. The binding data for SEQ ID NO:1 through SEQ ID NO:12 and native UPSEBP and rat SGP-1 presented in Table No. 1 were obtained as two data sets using a recent version of that sperm-egg binding assay in which the bound sperm were stained with a fluorescent dye binding to DNA and quantified using a fluorescent microwell-plate reader, by techniques known to those skilled in the art. The amino acid sequences of portions of human prosaposin (SEQ ID NO:15) and mouse prosaposin (SEQ ID NO:16) also are as shown.

A synthetic peptide having SEQ ID NO:1 provided sperm binding capability similar to that of native UPSEBP. Using nanomolar concentrations of SEQ ID NO:1, approximately twice as many sperm bound to the egg membrane substrate. The slightly shorter amino acid sequence of SEQ ID NO:2 had lower binding capability, and the very short SEQ ID NO:3 was essentially devoid of binding capability. The addition of amino acids distal to the terminal asparagine of SEQ ID NO:3 as embodied in SEQ ID NO:4 and SEQ ID NO:5 did not substantially change biological activity. Replacement of the terminal proline in SEQ ID NO:2 with a cysteine resulted in SEQ ID NO:6, with minimal change in biological activity relative to SEQ ID NO:2. Additions at the $NH_2$ end of an acetyl group in SEQ ID NO:7 or phenylalanine groups in SEQ ID NO:8 did not suppress biological activity relative to SEQ ID NO:2. SEQ ID NO:1 consistently gave greater biological activity than SEQ ID NO:2 through SEQ ID NO:8.

Substitutions of threonine at amino acid number six in SEQ ID NO:1 by proline resulted in SEQ ID NO:9, which also had very high biological activity, approximately equal to that of SEQ ID NO:1. The addition of L-leucine to the $NH_2$ end of SEQ ID NO:1 resulted in SEQ ID NO:10 and addition of D-leucine to the $NH_2$ end of SEQ ID NO:1 resulted in SEQ ID NO:11. The binding activity of SEQ ID NO:10 with the natural form of leucine was greater than that of SEQ ID NO:11 although both of these sequences had reduced activity relative to SEQ ID NO:1.

A synthetic peptide which embodied the complete intervening sequence between rat saposin A and saposin B was prepared as SEQ ID NO:12. SEQ ID NO:12 was studied in two forms. As synthesized, SEQ ID NO:12 had a linear, reduced form with SH-groups on the two terminal cysteine amino acids; in this linear form SEQ ID NO:12 had substantial biological activity and induced binding activity at 0.002 nM and, thus, had a potency approximately 90 times that of SEQ ID NO:9, which is entirely embodied in SEQ ID NO:12, or approximately 85 times the potency of SEQ ID NO:1. Induced oxidation of the SH-groups in SEQ ID NO:12 modified it to a hairpin, or closed loop, form with an —S—S-linkage between the two terminal cysteine amino acids. In this hairpin form SEQ ID NO:12 had enhanced biological activity and induced binding activity at 0.0004 nM and, thus, had 5 times the activity of the linear form of SEQ ID NO:12 and 425 times the activity of SEQ ID NO:1. Clearly, the hairpin form of SEQ ID NO:12 was more active than the linear form and, thus, tertiary structure as well as amino acid sequence are important for binding of sperm to egg membranes by the molecule which is the subject of this invention.

The amino acid sequences of rat SGP-1 and human or mouse prosaposins partially presented in Table 1 indicate that most of the SGP-1 or prosaposin molecule is not essential for sperm-egg binding activity. Furthermore, the portion of the prosaposin molecule with a sequence similar to that of SEQ ID NO:1 or SEQ ID NO:9 is an intervening sequence proteolytically cleaved during processing of prosaposin, namely the distal portion of the intervening sequence between saposin A and saposin B. Sequences integral to any of the saposins (A, B, C or D) are not necessary for the biological activity of SEQ ID NO:1 or SEQ ID NO:9. SEQ ID NO:12 extends the intervening sequence between saposin A and saposin B for 6 amino acids in the $NH_2$ direction into saposin A and for 4 amino acids in the COOH direction into saposin B. These extensions provide the terminal cysteines which are essential for formation of the hairpin loop form of SEQ ID NO:12. SEQ ID NO:5 combines the initial portion of saposin B with the terminal portion of the intervening sequence between saposin A and saposin B with virtually no biological activity.

Native or synthetic UPSEBP is useful for the following applications: a) as a pro-fertility additive to fluids used to suspend or resuspend sperm at some point in the processing of semen for artificial insemination or for in vitro fertilization or similar assisted reproductive technology; b) as the active ingredient for a vaginal pro-fertility medication for self administration; c) as the basis for analogs containing the epitopes providing sperm binding but with sequences prohibiting successful binding to the egg investments for contraception; d) as the basis for a reagent for use in quantifying the amount of UPSEBP present on sperm to provide information related to the potential fertility of an individual spermatozoon or the population of sperm in a seminal sample; and e) as the antigen for the production of antibodies useful in predicting potential fertility.

In one embodiment, native or synthetic UPSEBP is used to improve the capacity of fresh or frozen-thawed sperm to fertilize eggs. Prior to artificial insemination, an aliquot of fresh or frozen-thawed sperm is mixed with the native or synthetic UPSEBP which increases fertilizing capacity of the sperm.

In another embodiment, native or synthetic polypeptide can be used as a pro-fertility medication to be administered intra-vaginally as a semi-solid, liquid, or foam shortly before coitus. The medication might contain any of SEQ ID NO:1, SEQ ID NO:9, SEQ ID NO:10, SEQ ID NO:12, SEQ ID NO:13 or native UPSEBP as the active ingredient, suspended in an appropriate carrier which maintains biological activity, provides appropriate dispersion near the external cervical os, and facilitates effective and rapid partition of the active ingredient to the sperm after ejaculation.

Analogs of the essential sequence within UPSEBP, such as SEQ ID NO:1, SEQ ID NO:9, SEQ ID NO:12, or SEQ ID NO:13, which contain the epitope(s) binding the molecule to sperm, and also contain alternative sequences which prohibit rather than facilitate binding, are useful for their contraceptive effect on sperm. A contraceptive medication containing the analog is administered intra-vaginally as a semi-solid, liquid, or foam shortly before coitus. The medication containing a UPSEBP analog is suspended in an appropriate carrier which maintains biological activity and facilitates appropriate dispersion near the external cervical os and effective and rapid partition of the active ingredient to the sperm after ejaculation.

In another embodiment, the amount of UPSEBP present on sperm prior to insemination is quantified and is predictive of fertilizing potential. Synthetic sequences such as SEQ ID NO:1, SEQ ID NO:9, SEQ ID NO:12, or SEQ ID NO:13 are used as the basis for a reagent used in quantifying the amount of UPSEBP present on sperm to provide information related to potential fertility of individual sperm or the population of sperm in a seminal sample. UPSEBP apparently binds to sperm in a stoichiometric manner until saturation is reached. Exposure of sperm to the labeled molecule enables quantification of unoccupied sperm sites for binding UPSEBP and, indirectly, the number of UPSEBP molecules which had been present on the sperm. The synthetic sequence (such as SEQ ID NO:1, SEQ ID NO:9, SEQ ID NO:12, or SEQ ID NO:13) of UPSEBP is conjugated with fluorescein isothiocyanate, Texas Red, or other cyanine dyes, each of which fluoresces with a characteristic emission wavelength and intensity when excited with light of the proper wavelength. A suspension of sperm is exposed to an excess of labeled SEQ ID NO:1, for example, for approximately 5 minutes to enable binding, and then diluted >1:10,000 and passed through a flow cytometer for quantification of the amount of SEQ ID NO:8 bound by each of 3,000 to >10,000 sperm representative of those in the sample. A distribution profile can be made for the percentages of sperm in the sample lacking or having enough UPSEBP prior to analysis, with the latter likely to have a high fertilizing potential. Similar use could be made of a synthetic sequence or UPSEBP labeled with a light-absorbing reporter.

In yet another embodiment, the invention encompasses antigens for production of antibodies useful in predicting potential fertility of sperm. Natural or recombinant/synthetic UPSEBP or an analog thereof can be used to produce monoclonal or polyclonal antibodies against one or more epitopes of UPSEBP exposed while the molecule is bound by sperm. Antibodies against SEQ ID NO:6 and SEQ ID NO:12 have been produced and tested for use in such assays. Alternatively, a primary antibody against SEQ ID NO:13, for example, can be cleaved into Fab-fragments, which then can be directly labeled with a fluorescent cyanine dye before binding to the sperm. Samples containing a high percentage of sperm which bind a large amount of antibody have high fertilizing potential. Conversely, samples in which most sperm lacked typical amounts of UPSEBP would have poor fertilizing potential. In this embodiment, appropriate antibodies (or fragments thereof) are labeled with a fluorescent or light-absorbing reporter group and then used as a reagent to quantify the number of UPSEBP molecules present on each member of a population of sperm. The sperm treated with labeled Fab-fragments of antibody can be placed into an automated image analysis system in which both movement characteristics of individual sperm are quantified according to technologies known to those skilled in the art, and concurrently the number of exposed binding sites for UPSEBP on each spermatozoon is determined on the basis of fluorescence as disclosed herein. The resulting data establish a multidimensional distribution profile for the percentages of sperm in the sample lacking or having enough UPSEBP prior to analysis to have a high fertilizing potential, and also the motion characteristics of each cell in terms such as velocity, head yaw or wobble, and linearity of motion. Such a multi-vector analysis of each individual member of the sample population is predictive of potential fertility of that sample.

Although the invention has been described generally above, particular examples give additional illustration of the products and method steps typical of the present polypeptide and uses thereof. The data presented in FIGS. 1 to 3 and 6 to 9 show the number of sperm bound per unit area of laid hen's egg perivitelline membrane, or data derived from such binding, or bound to a substrate prepared using an extract from such perivitelline membranes pursuant to the method disclosed in co-pending patent application Ser. No. 08/234,448 abandoned. Except when noted, native protein extracted from rooster sperm with UPSEBP activity was used.

EXAMPLE 1

Restoration of Sperm Binding Capability

Freshly collected rooster sperm were cryopreserved, thawed and processed to remove glycerol. One portion of the thawed sperm received crude UPSEBP at a concentration of 2 µg protein per $10^6$ sperm. Samples containing 1–10×$10^6$ sperm were placed into wells coated with an extract of hen's egg membrane and incubated 180 minutes. Non-bound sperm were removed by washing, and bound sperm were stained with diamido-2-phenylindole and counted using an epifluorescent microscope. The results presented in FIG. 1 demonstrate the ability of UPSEBP to restore the capability of frozen-thawed rooster sperm to bind to hen's egg membrane protein in comparison to unprocessed sperm.

EXAMPLE 2

Comparison of UPSEBP to SGP-1 and Human Saposins

The procedures of Example 1 were repeated using SGP-1 and human saposins A, B, C and D. FIG. 2 shows that exposure of frozen-thawed sperm to SGP-1 restored binding to ≧100 percent of that obtained by exposure of other aliquots of the same sample of frozen-thawed sperm to UPSEBP (2 µg/million sperm) and that human saposin B restored binding to about 70 percent of the level achieved using UPSEBP. Saposins A, C and D were ineffective at restoring binding.

EXAMPLE 3

Ability of Polyclonal Antibodies to Neutralize Sperm-egg Binding

Figure 3:
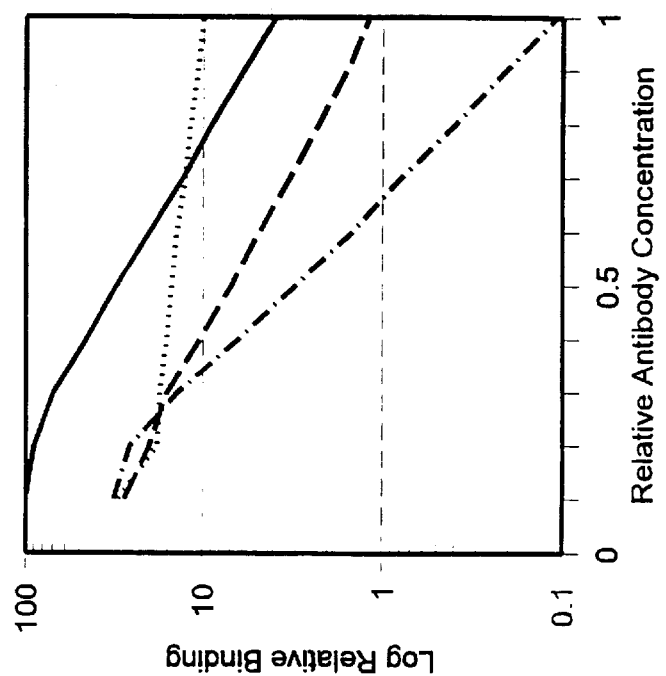
FIG. 3 compares the reduction in number of rooster sperm bound after treatment of sperm with polyclonal antibody against rat SGP-1, saposins A, B, C and D, and a portion of the intervening sequence between saposin A and saposin B.

Polyclonal antibodies against rat SGP-1, human saposins and a portion of the intervening sequence between saposin A and saposin B were provided by others who had prepared the antibodies by techniques known in the art. Antibody and 12.5×$10^6$ sperm were incubated for 15 minutes at room temperature. Sperm binding was determined as in Example 1. As shown in FIG. 3, antibodies against the intervening A-B sequence, saposin B and SGP-1 were very effective in eliminating activity of UPSEBP. Antibody against saposin A was less effective, and antibodies against saposins C and D had no effect.

EXAMPLE 4

Ability of UPSEBP to Improve Fertility of Frozen Thawed Rooster Sperm

Figure 4:
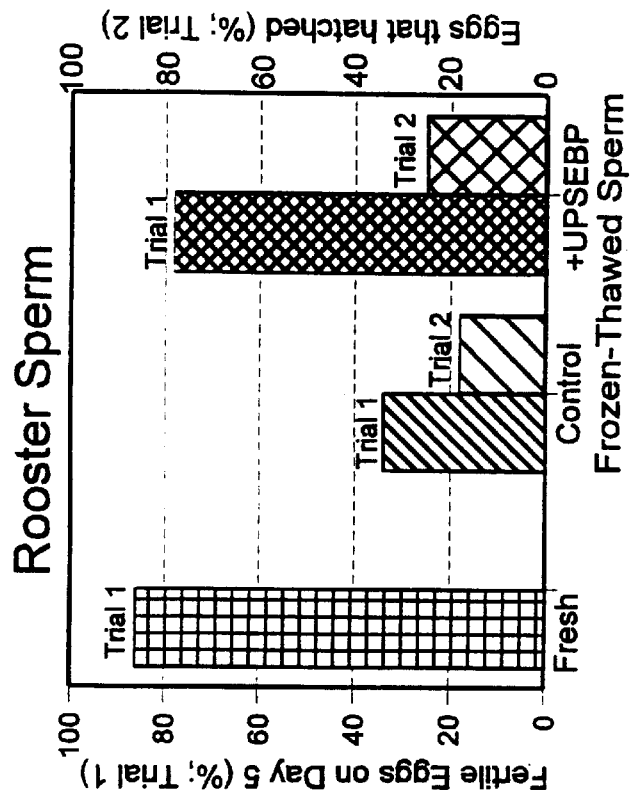
FIG. 4 compares the percentages of eggs which were fertilized (Trial 1) and hatched to provide a chick (Trial 2), laid by hens artificially inseminated with fresh sperm, frozen-thawed sperm and treated frozen-thawed rooster sperm.

Sperm in a sample of pooled semen were used to obtain fertility data before cryopreservation (i.e., fresh) and after cryopreservation and post-thaw processing to slowly remove glycerol (frozen-thawed). One portion of the thawed sperm was suspended in Minnesota-A buffer alone, and the second was treated with Minnesota-A buffer containing crude UPSEBP at 2 µg protein per $10^6$ sperm. As shown in FIG. 4, fertility of the sperm processed in UPSEBP was double that for sperm not treated with UPSEBP and approached the level of fresh sperm. Hatchability of eggs artificially fertilized by sperm treated with UPSEBP increased from 18 to 25 percent.

EXAMPLE 5

Ability of UPSEBP to Improve Fertility of Fresh Rooster Sperm

Figure 5B:
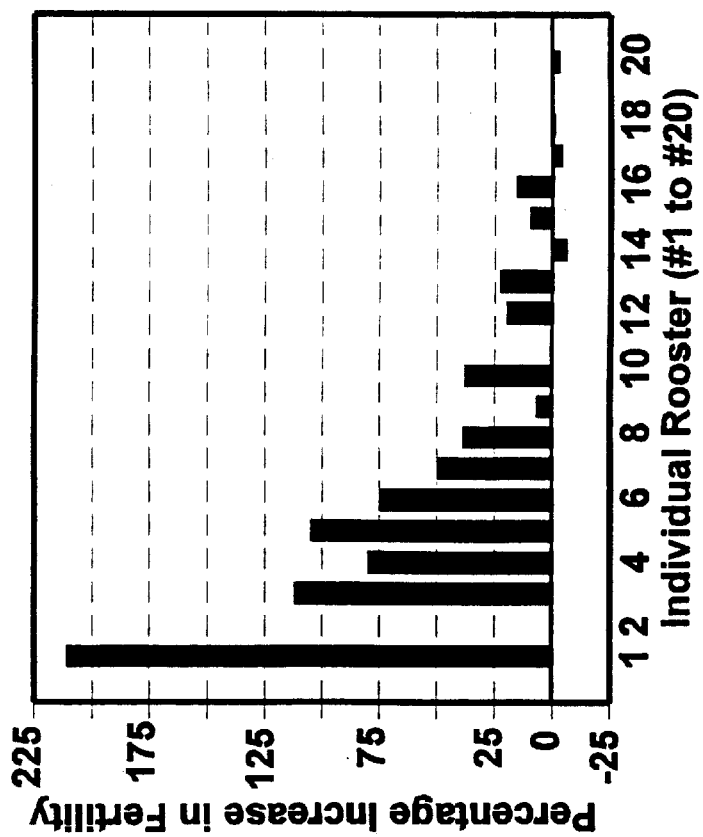
Figure 5A:
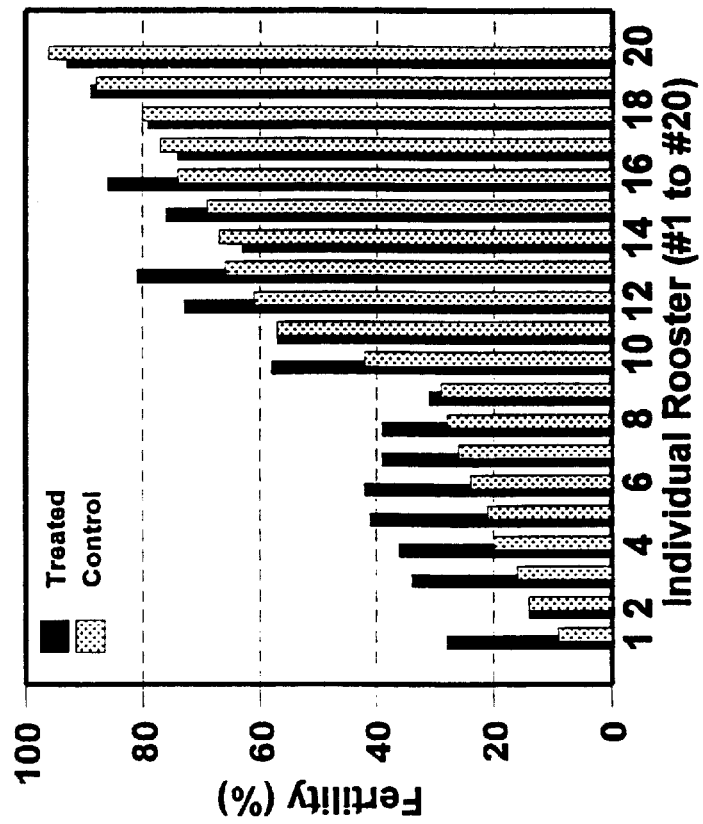
FIG. 5a shows the fertility of 20 individual roosters, as the percentage of eggs laid providing a living chick, when 18 hens/male were inseminated with fresh sperm and 18 other hens/male were inseminated with treated fresh sperm from the same ejaculate, with 3 replicate inseminations.

Fresh sperm from 20 individual roosters were divided into two aliquots: one remained untreated, and the other was treated with native rooster UPSEBP at 0.04 µg protein per $10^6$ sperm. The percent fertility (percentage of ~200 laid eggs which resulted in a live chick) and percent increase in fertility over untreated sperm was determined and is depicted in FIGS. 5*a* and 5*b*. For 8 out of the 20 roosters tested, the addition of UPSEBP resulted in more than a 25 percent increase in fertility, and for another 5 of the 20 roosters, there was a 7 to 23 percent increase in fertility. The rooster sperm with lower natural levels of fertility were most benefited by treatment with UPSEBP.

EXAMPLE 6

Amount of UPSEBP

Figure 6:
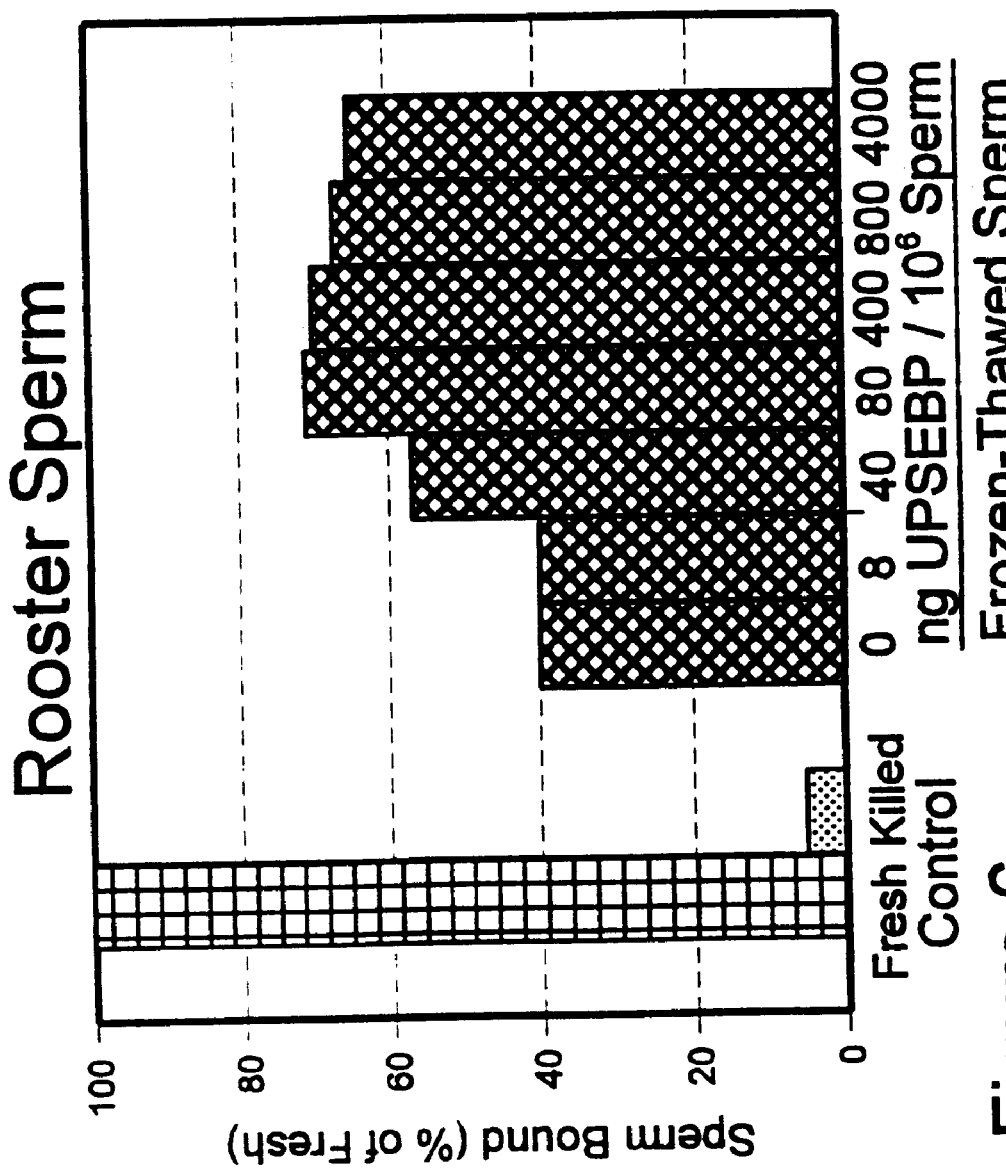
FIG. 6 shows ranges of amounts of UPSEBP (crude extract of native protein) which partially restored binding capability to frozen-thawed rooster sperm.

Rooster sperm subjected to a cryopreservation cycle were treated with increasing amounts of partially purified UPSEBP and subject to a standard binding assay, together with aliquots of unfrozen (fresh) sperm. FIG. 6 shows that treatment of frozen-thawed rooster sperm with 0.04–4.0 µg UPSEBP per $10^6$ sperm partially restored the sperm's capability to bind to the membrane of a hen's egg.

EXAMPLE 7
UPSEBP Across Poultry Species

Figure 7A:
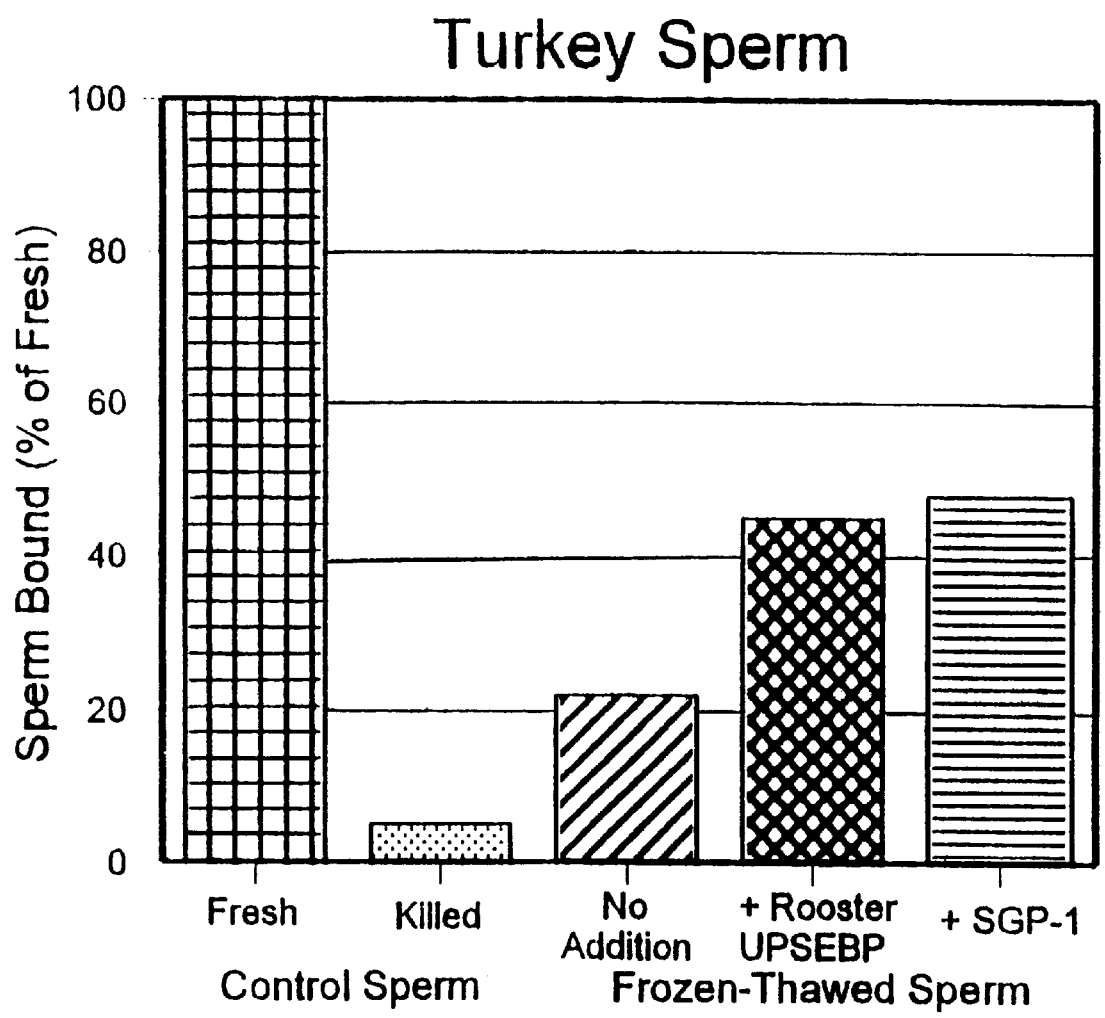
FIG. 7a shows the restorative capability of rooster UPSEBP (native protein extracted from rooster sperm) and rat SGP-1 on binding of thawed cryopreserved turkey sperm.
Figure 7B:
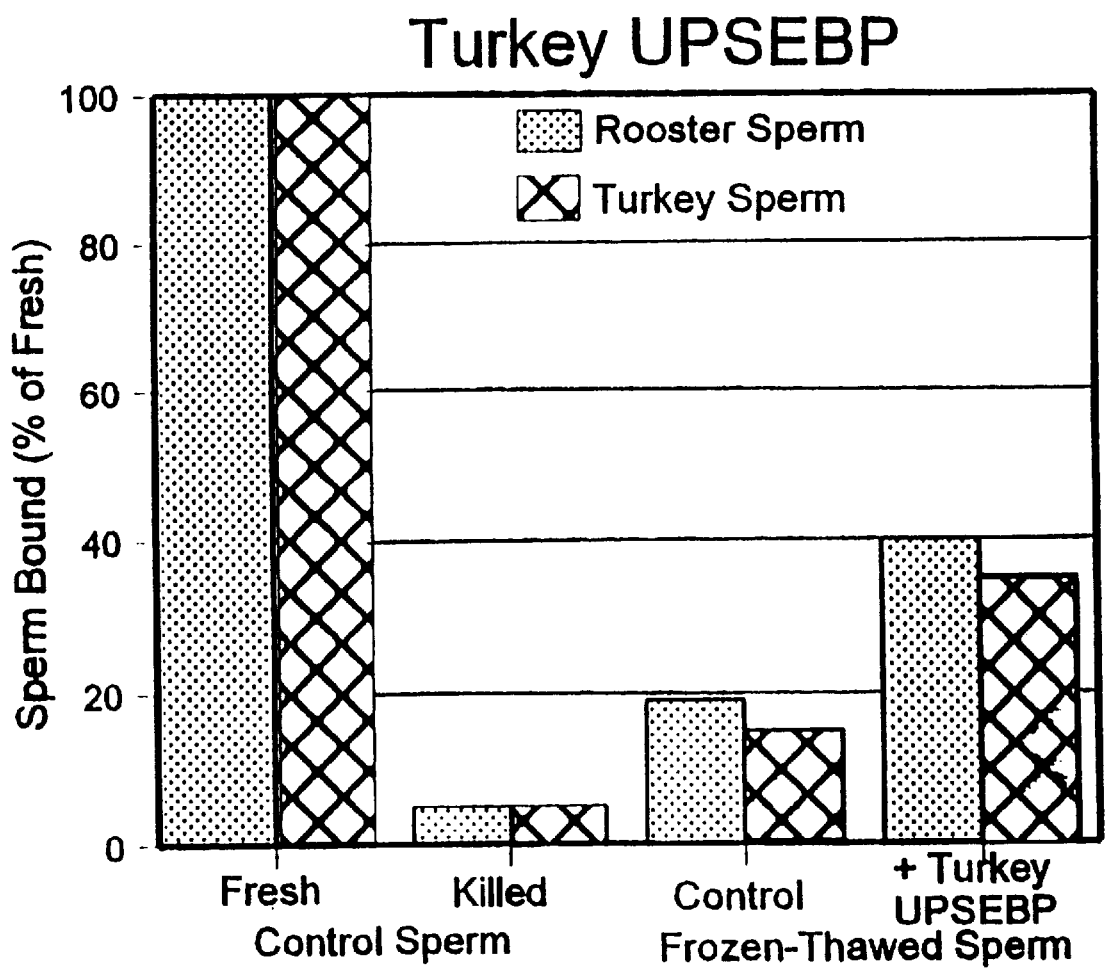
FIG. 7b shows the restorative capability of turkey UPSEBP (native protein extracted from turkey sperm) on binding of thawed cryopreserved rooster sperm and thawed cryopreserved turkey sperm.

Frozen-thawed turkey sperm were exposed to rooster UPSEBP or semi-purified SGP-1. Treatment of thawed frozen turkey sperm with rooster UPSEBP partially restored the capability of sperm to bind to a membrane of a hen's egg as depicted in FIG. 7a. Turkey UPSEBP, prepared in a manner similar to that used to prepare native rooster UPSEBP, also partially restored the capability of binding the turkey sperm or rooster sperm to chicken egg membrane protein, as depicted in FIG. 7b.

EXAMPLE 8
Treatment of Stored Turkey Sperm

Figure 8:
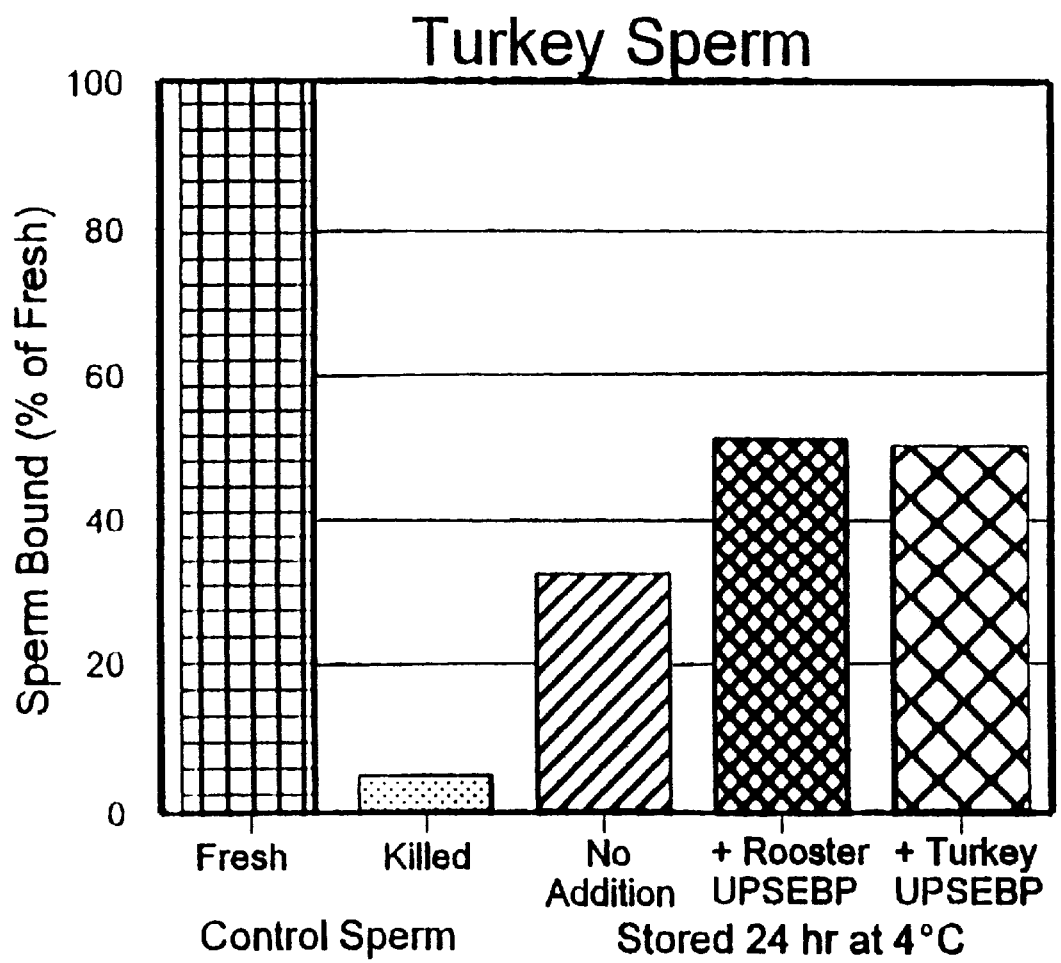
FIG. 8 shows the capability of rooster UPSEBP and turkey UPSEBP to restore the binding of turkey sperm stored at 4° C. for 24 hours.

Turkey sperm were stored for 24 hours at 4° C. Samples of the stored sperm were untreated or treated with 2 μg protein per $10^6$ sperm of rooster UPSEBP or turkey UPSEBP. Samples of the treated and non-treated sperm were tested at $2.5 \times 10^6$ sperm/well for their capacity to bind chicken's egg membrane preparations together with samples of fresh or killed sperm. As shown in FIG. 8, after 24 hours the untreated sperm had depressed binding relative to the fresh sperm (0 hr.), and treatment with either rooster or turkey UPSEBP partially restored binding.

EXAMPLE 9
Treatment of Stallion Sperm

Figure 9:
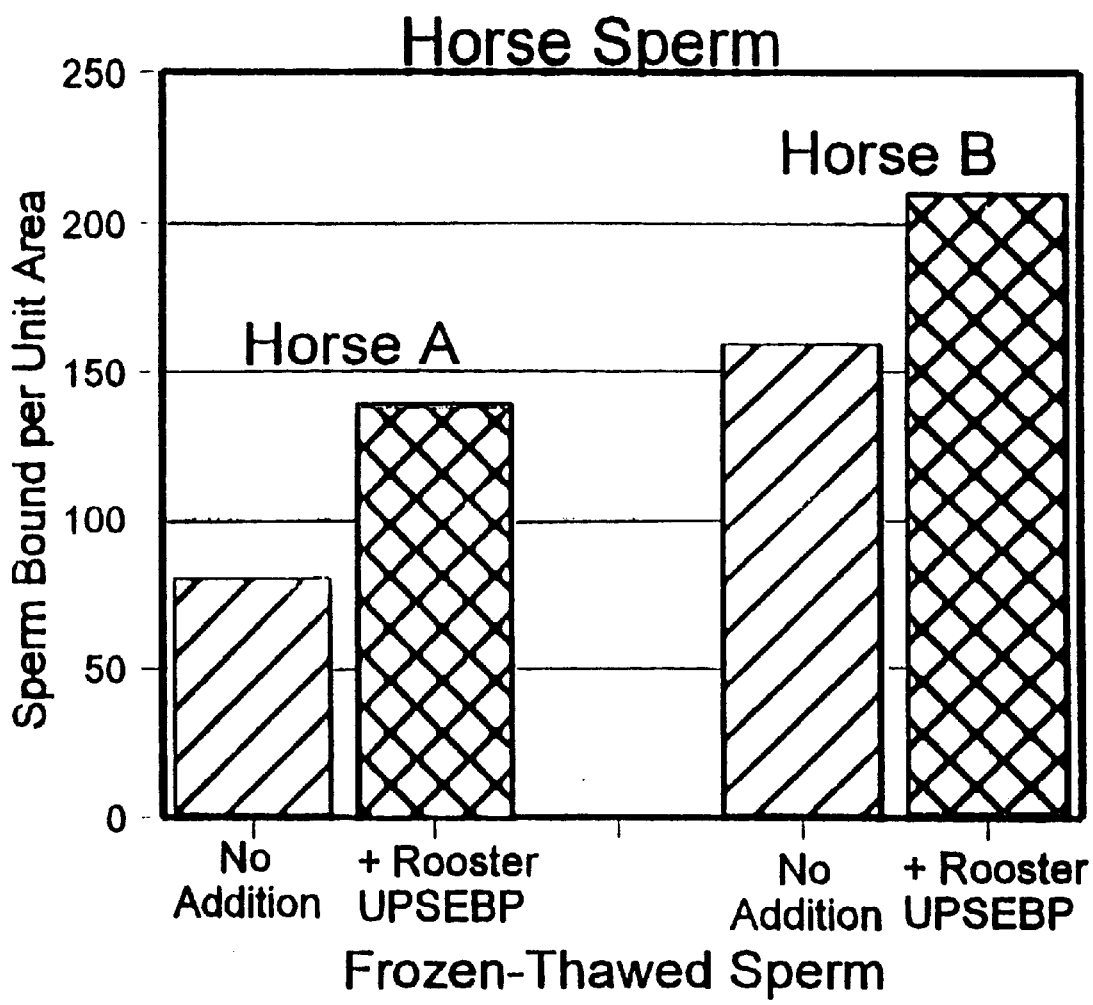
FIG. 9 shows the restorative capability of rooster UPSEBP (native protein extracted from rooster sperm) on binding of thawed cryopreserved stallion sperm.

The ability of rooster UPSEBP to enhance binding of frozen-thawed stallion sperm to a chicken egg membrane preparation was evaluated. Sperm from two stallions of unknown fertility were frozen by a conventional procedure. One portion of each sample received no supplement, while a second portion received 2 μg rooster UPSEBP per $10^6$ sperm. FIG. 9 shows that for both seminal samples, rooster UPSEBP was effective in increasing the percentage of stallion sperm bound to hen's egg membrane.

EXAMPLE 10
Antibody

A primary antibody was produced in two rabbits against SEQ ID NO:5, linked via the cysteine amino acid to keyhole limpet, with use of standard adjuvants and techniques. The immune serum was harvested and used as a primary antibody to label rooster sperm, fixed in low ionic strength buffer using paraformaldehyde and processed by standard techniques, after which fluorescein isothiocyanate-labeled goat-antisheep gama globulin was used as a second antibody. Analyses by flow cytometry revealed the percent of sperm as labeled, and visual examinations by epifluorescence microscopy revealed localization of the antibodies to the head region. A similar antibody was prepared against SEQ ID NO:12.

Although the invention has been described with particularity in the above text and examples, the invention is only to be limited insofar as is set forth in the accompanying claims.

TABLE 1

SEQUENCE COMPARISON OF SYNTHETIC PEPTIDES (SEQ ID NOS: 1 TO 13) WITH RAT SGP-1 (SEQ ID NO: 14), HUMAN PROSAPOSIN (SEQ ID NO: 15) AND MOUSE PROSAPOSIN (SEQ ID NO: 16) AND DATA ON IN VITRO BINDING OF FROZEN-THAWED ROOSTER SPERM TREATED WITH PEPTIDES TO AN EXTRACT OF HEN'S EGG MEMBRANE BOUND TO WELLS OF A MICROWELL PLATE†

| SEQ ID NO. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| AMINO ACID SEQ. | | | | | | | | | | | | | | Pro | Pro | Pro |
| | | | | | | | | | | | | | | Gly | Gly | Gly |
| | | | | | | | | | | | | | | Glu | Glu | Glu |
| | | | | | | | | | | | | | | Val | Val | Val |
| | | | | | | | | | | | | | | Cys | Cys | Cys |
| | | | | | | | | | | | | | | Ala | Ala | Ala |
| | | | | | | | | | | | | | | Leu | Leu | Leu |
| | | | | | | | | | | | | | | Asn | Asn | Asn |
| | | | | | | | | | | | | | | Leu | Leu | Leu |
| | | | | | | | | | | | | Cys | Cys | Cys | Cys | Cys |
| | | | | | | | | | | | | Gln | Glu | Gln | Glu | Gln |
| | | | | | | | | | | | | Ser | Ser | Ser | Ser | Ser |
| | | | | | | | | | | | | Leu | Leu | Leu | Leu | Leu |
| | | | | | | | | | | | | Gln | Gln | Gln | Gln | Gln |
| | | | | | | | | | | | | Glu | Lys | Glu[c] | Lys[c] | Glu[c] |
| | | | | | | | | | | | | Tyr | His | Tyr[d] | His[d] | Tyr[d] |
| | | | | | | | | | | | | Leu | Leu | Leu | Leu | Leu |
| | | | | | | | | | | | | Ala | Ala | Ala | Ala | Ala |
| | | | | | | | | | | | | Glu | Glu | Glu | Glu | Glu |
| | | | | | | | | | | | | Gln | Leu | Gln | Leu | Gln |
| | | | | | | | | | | | | Asn | Asn | Asn | Asn | Asn |
| | | | | | | | | | | | | | His | | His | |
| | | | | | | | | | | | | Gln | Gln | Gln | Gln | Gln |
| | | | | | | | | | | | | Arg | Lys | Arg | Lys | Lys |
| | | | | | | | | | | | | Gln | Gln | Gln | Gln | Gln |
| | | | | | | | | | | | | Leu | Leu | Leu | Leu | Leu |
| | | | | | | | | | | | | Glu | Glu | Glu | Glu | Glu |
| | | | | | | | | | | | | Ser | Ser | Ser | Ser | Ser |
| | | | | | | | | | | | | Asn | Asn | Asn | Asn | Asn |
| | | | | | | | | | | | | Lys | Lys | Lys | Lys | Lys |
| | | | | | | | | | | | | Ile | Ile | Ile | Ile | Ile |
| | | | | | | | | | | | | Pro | Pro | Pro | Pro | Pro |
| | | | | | | | | | | | | Glu | Glu | Glu | Glu | Glu |
| | | | | | | | | | | | | Val | Leu | Val | Leu | Val |
| | | | | | | | | | | | | Asp | Asp | Asp | Asp | Asp |

TABLE 1-continued

SEQUENCE COMPARISON OF SYNTHETIC PEPTIDES (SEQ ID NOS: 1 TO 13) WITH RAT SGP-1 (SEQ ID NO: 14), HUMAN PROSAPOSIN (SEQ ID NO: 15) AND MOUSE PROSAPOSIN (SEQ ID NO: 16) AND DATA ON IN VITRO BINDING OF FROZEN-THAWED ROOSTER SPERM TREATED WITH PEPTIDES TO AN EXTRACT OF HEN'S EGG MEMBRANE BOUND TO WELLS OF A MICROWELL PLATE†

| SEQ ID NO. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| | | | | | | | | | | | | Leu | Met | Leu | Met | Met |
| | | | | | | | | | | | | Ala | Thr | Ala | Thr | Ala |
| | | | | | | | | | | | | Arg | Glu | Arg | Glu | Arg |
| | | | | | | | | | | | | Val | Val | Val | Val | Val |
| | | | | | | | | | | | | Val | Val | Val | Val | Val |
| | | | | | | | | | | | | Ala | Ala | Ala | Ala | Ala |
| | | | | | | | | | | | | Pro | Pro | Pro | Pro | Pro |
| | | | | | | | | | | | | Phe | Phe | Phe | Phe | Phe |
| | | | | | | | | | | | | Met | Met | Met | Met | Met |
| | | | | | | | | | | | | Ser | Ala | Ser | Ala | Ser |
| | | | | | | | | | | | | Asn | Asn | Asn | Asn | Asn |
| | | | | | | | | | | | | Ile | Ile | Ile | Ile | Ile |
| | | | | | | | | | | | | Pro | Pro | Pro | Pro | Pro |
| | | | | | | | | | | | | Leu | Leu | Leu | Leu | Leu |
| | | | | | | Phe | | | | | | Leu | Leu | Leu | Leu | Leu |
| | | | | | | Phe | | | | L-Leu | D-Leu | Leu | Leu | Leu | Leu | Leu |
| | Tyr | Tyr | | | | | Tyr | Acetyl Tyr | Tyr | Tyr | Tyr | Tyr | Tyr | Tyr | Tyr | Tyr | Tyr |
| | Pro | Pro | | | | Pro | Pro | Pro | Pro | Pro | Pro | Pro | Pro | Pro | Pro | Pro |
| | Gln | Gln | | | | Gln | Gln | Gln | Gln | Gln | Gln | Gln | Gln | Gln | Gln | Gln |
| | Asp | Asp | | | | Asp | Asp | Asp | Asp | Asp | Asp | Asp | Asp | Asp | Asp | Asp |
| | Arg | Arg | | | | Arg | Arg | Arg | Arg | Arg | Arg | Arg | Gly | Arg | Gly | His |
| | Thr | Thr | | | | Thr | Thr | Thr | Pro | Thr | Thr | Pro | Pro | Pro | Pro | Pro |
| | Arg | Arg | | | | Arg | Arg | Arg | Arg | Arg | Arg | Arg | Arg | Arg | Arg | Arg |
| | Ser | Ser | | | | Ser | Ser | Ser | Ser | Ser | Ser | Ser | Ser | Ser | Ser | Ser |
| | Gln | Gln | Gln | Gln | | Gln | Gln | Gln | Gln | Gln | Gln | Gln | Lys | Gln | Lys | Gln |
| | Pro | Pro | Pro | Pro | Pro | Pro | Pro | Pro | Pro | Pro | Pro | Pro | Pro | Pro | Pro | Pro |
| | Gln | Gln | Gln | Gln | Gln | Gln | Gln | Gln | Gln | Gln | Gln | Gln | Gln | Gln | Gln | Gln |
| | Pro | Pro | Pro | Pro | Pro | Cys | Pro | Pro | Pro | Pro | Pro | Pro | Pro | Pro | Pro | Pro |
| | Lys | | Lys | Lys | | | | | Lys | Lys | Lys | Lys | Lys | Lys | Lys | Lys |
| | Ala | | Ala | Ala | | | | | Ala | Ala | Ala | Ala | Asp | Ala | Asp | Ala |
| | Asn | | Asn | Asn | | | | | Asn | Asn | Asn | Asn | Asn | Asn[e] | Asn[e] | Asn[e] |
| | | | Glu | Glu | | | | | | | | Glu | Gly | Glu[f] | Gly[f] | Glu[f] |
| | | | Asp | Asp | | | | | | | | Asp | Asp | Asp | Asp | Asp |
| | | | Val | Val | | | | | | | | Val | Val | Val | Val | Val |
| | | | Cys | Cys | | | | | | | | Cys | Cys | Cys | Cys | Cys |
| | | | Gln | Gln | | | | | | | | | | Gln | Gln | Gln |
| | | | Asp | Asp | | | | | | | | | | Asp | Asp | Asp |
| | | | Cys | Cys | | | | | | | | | | Cys | Cys | Cys |
| | | | Met | Met | | | | | | | | | | Met | Ile | Met |
| | | | | Lys | | | | | | | | | | Lys | Gln | Lys |
| | | | | Leu | | | | | | | | | | Leu | Met | Leu |
| | | | | Val | | | | | | | | | | Val | Val | Val |
| | | | | Thr | | | | | | | | | | Thr | Thr | Ser |
| | | | | Asp | | | | | | | | | | Asp | Asp | Asp |
| | | | | | | | | | | | | | | Ile | Ile | Val |
| PEPTIDE CONCENTRATION[a] | 0.17 | 300 | 2,125 | 85 | 510 | 370 | 50 | 100 | 0.18 | 8.8 | 25 | * | | 1.0 | Unk | Unk |
| ACTIVITY[b] | 1 | 0.0006 | 0.0001 | 0.002 | 0.0003 | 0.0005 | 0.003 | 0.002 | 0.94 | 0.94 | 0.001 | | | 0.17 | Unk | Unk |

[a]Concentration of peptide (nanomolar) which, after tenfold dilution of the sperm suspension, provided maximum binding.
[b]Activity relative to SEQ ID NO: 1.
[c]End of saposin A.
[d]Start of intervening sequence between saposin A and saposin B.
[e]End of intervening sequence between saposin A and saposin B.
[f]Start of saposin B.
†Maximum binding obtained with the native molecule in a semipurified extract from rooster sperm gave a value of 80 sperm (fluorescent) equivalent units/unit area; concentration of the active molecule in the extract is unknown, but assuming MW = 10,000 and purity of 0.1% the mass used would have made a 1 nM solution. Sperm treated with SEQ ID NO: 1 gave a value of 76 sperm (fluorescent) equivalent units/unit area as compared to a value of 40 for untreated control sperm, and values for other sequences ranged from −40 to 141 sperm (fluorescent) units/unit area at the designated concentration of peptide. Amino acids in rat SGP-1 (prosaposin; Collard et al., 1988) are compared with those in human prosaposin (O'Brien & Kishimoto, 1991; Kishimoto et al., 1992) and mouse prosaposin (Tsuda et al., 1992).
*SEQ ID NO: 12 was studied in two forms: (1) as synthesized, in a linear reduced form with SH-groups in the two terminal cysteines, and (2) modified, to a hairpin oxidized form with an -S-S-linkage between the two terminal cysteines, induced by oxidation of the SH-groups. As a linear, reduced, 60 amino acid molecule, SEQ ID NO: 12 was active at 0.002 nM and, thus, had ~85 times the potency of SEQ ID NO: 1. As a hairpin, oxidized, 60 amino acid molecule, however, SEQ ID NO: 12 was active at 0.0004 nM and, thus, had 425 times the potency of SEQ ID NO: 1. Thus, the biological activity of SEQ ID NO: 12 was dependent on its tertiary structure, with bioactivity activity of the hairpin loop form ~5 times that of the linear form.

What is claimed is:

1. A method of enhancing sperm-egg binding comprising the steps of:

contacting a quantity of sperm with a quantity of purified amino acid polypeptide, said purified amino acid polypeptide having a sequence defined in part by a truncated portion of a prosaposin molecule, wherein said polypeptide has at least one active site which binds to said sperm by way of a sperm plasma membrane thereon; and contacting said sperm contacted with said polypeptide with investments of one or more oocytes.

2. The method according to claim 1 herein said polypeptide is a synthetic polypeptide.

3. The method according to claim 2 wherein said polypeptide comprises a sequence selected from the group consisting of SEQ ID NO: 1, SEQ ID NO: 9, SEQ ID NO: 12, SEQ ID NO: 13, and a corresponding prosaposin sequence from an alternative species.

4. The method according to claim 2 wherein said quantity of polypeptide is added to an aqueous suspension of said sperm to create an admixture prior to exposing an aliquot of said admixture to at least one oocyte.

5. The method according to claim 3 wherein said quantity of polypeptide is added to an aqueous suspension of said sperm to create an admixture prior to exposing an aliquot of said admixture to at least one oocyte investment.

6. The method according to claim 4 wherein said aqueous suspension is cryopreserved and subsequently thawed prior to adding said quantity of polypeptide thereto.

7. The method according to claim 5 wherein said admixture is cryopreserved and subsequently thawed prior to exposing an aliquot of said admixture to at least one oocyte.

8. The method according to claim 4 wherein said aliquot of said admixture is exposed to at least one oocyte by administering said aliquot intravaginally, intracervically, or by intrauterine insertion in a female in which fertilization of said at least one oocyte is desired.

9. The method according to claim 7 wherein said aliquot of said admixture is exposed to at least one oocyte by administering said aliquot intravaginally, intracervically, or by intrauterine insertion in a female in which fertilization of said at least one oocyte is desired.

10. A method of enhancing sperm-egg binding comprising the steps of:

(a) inserting a quantity of purified amino acid polypeptide intravaginally into a female prior to coitus, said purified amino acid polypeptide having a sequence defined in part by a truncated portion of a prosaposin molecule, wherein said polypeptide has at least one active site which binds to said sperm by way of a sperm plasma membrane thereon;

(b) depositing an aliquot of an aqueous suspension of sperm intravaginally in said females;

(c) contacting said sperm deposited intravaginally with said quantity of purified amino acid polypeptide; and (d) contacting one or more oocytes in said female with said sperm contacted with said polypeptide.

* * * * *

UNITED STATES PATENT AND TRADEMARK OFFICE
CERTIFICATE OF CORRECTION

PATENT NO. : 6,004,586
DATED : December 21, 1999
INVENTOR(S) : Roy H. Hammerstedt et al.

It is certified that error appears in the above-identified patent and that said Letters Patent is hereby corrected as shown below:

Title Page, [54] title should read: "Method to Enhance Binding of Sperm to Egg Investments"

Column 1 Lines 1-5 title should read: "Method to Enhance Binding of Sperm to Egg Investments"

Column 3 Line 57 "cut off" should read --cut-off--.

Column 4 Lines 32-33 "were compared" should read --was compared--.

Column 6 Line 10 "self administration" should read --self-administration-- (insert hyphen).

Column 23 Line 3, Claim 2, "herein" should read --wherein--.

Signed and Sealed this

Fifth Day of December, 2000

Attest:

Q. TODD DICKINSON

*Attesting Officer*     *Director of Patents and Trademarks*